(12) United States Patent
Kepley

(10) Patent No.: US 7,947,262 B2
(45) Date of Patent: May 24, 2011

(54) USE OF FULLERENES FOR THE TREATMENT OF MAST CELL AND BASOPHIL-MEDIATED DISEASE

(75) Inventor: Chris Kepley, New Kent, VA (US)

(73) Assignee: Virginia Commonwealth University, Richmond, VA (US)

( * ) Notice: Subject to any disclaimer, the term of this patent is extended or adjusted under 35 U.S.C. 154(b) by 1019 days.

(21) Appl. No.: 11/535,196

(22) Filed: Sep. 26, 2006

(65) Prior Publication Data

US 2008/0107618 A1    May 8, 2008

(51) Int. Cl.
*A61K 39/395*    (2006.01)
*A61K 31/785*    (2006.01)
*A61K 31/44*     (2006.01)
*A61K 31/135*    (2006.01)
*A61K 31/137*    (2006.01)
*A61K 31/4025*   (2006.01)

(52) U.S. Cl. ............... 424/78.27; 424/178.1; 514/58; 514/277; 514/422; 514/649; 514/731

(58) Field of Classification Search ............... 424/78.27, 424/178.1; 514/58, 277, 422, 649, 731
See application file for complete search history.

(56) References Cited

U.S. PATENT DOCUMENTS

| | | | |
|---|---|---|---|
| 5,648,523 A | 7/1997 | Chiang | |
| 6,046,361 A | 4/2000 | Chiang | |
| 6,380,434 B1 | 4/2002 | Chiang | |
| 6,777,445 B2 * | 8/2004 | Lei et al. | 514/557 |
| 6,790,963 B2 | 9/2004 | Chiang et al. | |
| 2005/0136079 A1 * | 6/2005 | Burangulov et al. | 424/401 |
| 2005/0175541 A1 * | 8/2005 | Lanza et al. | 424/9.5 |

\* cited by examiner

*Primary Examiner* — James D Anderson
*Assistant Examiner* — Zohreh Vakili
(74) *Attorney, Agent, or Firm* — Whitham, Curtis, Christofferson & Cook, P.C.

(57) ABSTRACT

Mast cell (MC) and peripheral blood basophil (PBB)-associated diseases are treated or prevented, or their symptoms are alleviated by the administration of water soluble fullerenes (buckeyballs) to the individual under conditions sufficient to inhibit MC and PBB responses. MC and PBB responses are associated with, for example, various allergies including Type 1 hypersensitivity initiated by IgE-antigen, arthritis, multiple sclerosis, urticaria, atopic dermatitis, heart disease, etc. The treatment regimen can be enhanced using Chimeric fullerenes that specifically home to and inhibit MC and PBB cells. These molecules, for example, comprise fullerenes to which are attached IgE Fc or stem cell factor (SCF) peptides that bind to receptors specifically on MC and PBB cells. Additional molecules which may be used in the processes include IgE Fc or SCF peptides with several fullerenes covalently attached.

8 Claims, 9 Drawing Sheets

ND STATES PATENT

USE OF FULLERENES FOR THE TREATMENT OF MAST CELL AND BASOPHIL-MEDIATED DISEASE

BACKGROUND OF THE INVENTION

1. Field of the Invention

The invention generally relates to the treatment of mast cell (MC) and peripheral blood basophil (PBB)-associated diseases. In particular, the invention provides methods of using water soluble fullerene derivatives and targeted chimeric fullerenes to inhibit MC and PBB responses that cause allergic reactions, and other inflammatory diseases such as arthritis.

2. Background of the Invention

The Emerging Field of Nanomedicine

Nanomedicine is an emerging area of biomedical research that has potential for advancing medical science. This area of research entails the creation and use of materials at the level of molecules and atoms in order to investigate and treat diseases and disorders; generally less than 100 nM in size. The unique properties of nanomaterials, including single walled carbon nanotubes, fullerenes, quantum dots, and metal oxides, make them potential candidates for rational delivery and targeting of pharmaceutical, therapeutic, and agents for disease diagnosis, treatment, and prevention of a wide range of disease processes. Many of these molecules can be easily manipulated and functionalized by the addition of drugs or solubilizing groups within their cage structure or to their external walls and tips. This allows for specific homing to precise targets (cells, receptors, etc) related to clinical conditions to achieve the required response while minimizing side effects given their size.

The two most widely known forms of carbon include graphite and diamond. Fullerenes or "Buckyballs" represent the third allotrope of carbon[1]. In this form, for example, 60 or 70 carbon molecules are arranged in a cage structure and are water insoluble unless derivatized with various compounds (FIG. 1). The fullerene family, and especially $C_{60}$, has very appealing properties which can be exploited alone or through the addition of molecules within and on the outside of the cage structure.

Fullerenes also have the potential to deliver therapeutics given their desirable properties. Therapeutic and diagnostic agents can be encapsulated, covalently attached, or adsorbed on to different-sized fullerenes[2-5]. These strategies help to solve drug solubility issues which is a major pitfall for many drug screening initiatives where high-throughput screening identifies new drug candidates that are bypassed due to insolubility. Thus, fullerenes may induce the re-evaluation of many by-passed drug candidates.

The small size of fullerenes and their ability to be manipulated with synthetic polymers and ligands make them attractive for specific targeting of cells and locations within the body after intravenous or subcutaneous injection. There are many possibilities for using these molecules for new therapeutic applications and improving the efficacy of drugs already developed. For example, although most microorganisms are killed by macrophages, many pathogenic organisms have developed means for resisting macrophage destruction following phagocytosis. In certain cases, the macrophage lysosome and/or cytoplasm is the obligate intracellular home of the microorganism; examples include *Toxoplasma gondii*, various species of *Leishmania, Mycobacterium tuberculosis*, and *Listeria monocytogenes*. Passive targeting of nanoparticulate vehicles with encapsulated antimicrobial agents to infected macrophages is being investigated as a logical strategy for effective microbial killing[6]. In theory, the nanotubes act as a "Trojan horse" protecting the drug until it is released inside the cellular compartments. Adding macrophage-targeting moieties such as liposomes can increase the specificity and result in a highly specific drug delivery system.

Another field in which fullerenes are being investigated as providing new classes of drugs is in medical imaging (i.e. magnetic resonance imaging; MRI). Certain fullerenes can encapsulate metallic ions detected by imaging hardware and software while preventing the toxic metals from being absorbed into the reticuloendothelial system[7]. Nanomaterials are also being investigated as being highly sensitive biosensors. Moieties can be added to nanomaterials that can be activated by changes in the environmental pH, magnetic fields, light, and heat[4;8]. Given the plethora of capabilities and options that nanomaterials bring to the field of nanomedicine it is not surprising the effect it is having on medical research and drug delivery science[3].

The Effects of Fullerenes on Biological Systems

Given the relative infancy of the field, the studies examining the toxicity of fullerenes on human systems are still emerging. As with all new technologies the potential health risks for these and other nanoparticulate materials have been a concern largely due to the dearth of studies examining the effects these materials have on physiological systems. Toxicological studies mostly use uncharacterized, single wall carbon nanotubes, and the conclusions have been conflicting and inconclusive[9-13]. Water solubility, dose, exposure time, and similar parameters all appear to influence the cytotoxicity of the fullerenes.

Certain fullerenes have exhibited cytotoxic effects on human cells; whereas, other fullerene derivatives have not. Unfunctionalized $C_{60}$ appears to be cytotoxic in certain systems given its highly charged core structure. As more functional side chains, such as hydroxyl or carboxyl groups, are added to the fullerene skeleton, the level of cytotoxicity appears to diminish and water solubility increases[14;15]. Various studies have demonstrated that fullerenes have no cytotoxic effects on keratinocytes and can protect blood mononuclear cells and macrophages from oxidative stress[16-17]. Furthermore, non-derivatized, single wall carbon nanotubes showed a dose-dependent effect on pulmonary inflammation and fibrosis in mice[18] but had little effect on fibroblasts[15]. In addition to functionalization, the level of cytotoxicity also depends on the concentration of fullerenes exposed to cells. Yamawaki et al. showed the cytotoxic effects of hydroxyl fullerenes on endothelial cells using high concentrations[19]. In addition, high concentrations of fullerene-based amino acid nanoparticles were cytotoxic to epidermal keratinocytes, while low concentrations displayed no cytotoxic effects[20].

Fullerenes as Antioxidants

The term free radical refers to species that have momentarily accepted an extra electron which makes them highly reactive. The most common are referred to as reactive oxygen species (ROS). The ROS include free hydroxyl radicals (OH.), superoxide anions ($O_2^-$), singlet oxygen ($O_2$), hydrogen peroxide ($H_2O_2$) and several others. These ROS can react with, cross link and alter the function of many macromolecules. Reaction products whose presence is indicative of ROS activity include 8-hydroxyl guanisine, O-tyrosine or dityrosine (indicative of protein oxidation), and malondialdehyde (indicative of peroxidation damage to phospholoipids). These molecules can bind to/complex with other macromolecules and affect a wide variety of biological processes including apoptosis, DNA mutation that cause cancers, inflammation and tissue degeneration.

Anti-oxidants are molecules that absorb the free radical electron. Superoxide dismutases are a family of enzymes that convert superoxide anion into hydrogen peroxide which is then converted into water by another enzyme, catalase. Other anti-oxidants include glutathione, Vitamins A, C, and E, and bioflavanoids.

The fullerene core can react with free radical species given its capacity to absorb electrons and disperse them through the twenty benzene rings distributed over its surface. In fact it is one of the most potent free radical scavengers known with the potential for being "sponges" in diseases involving ROS[21]. This property makes them attractive therapeutic options in acute and chronic neurodegenerative diseases such as Parkinson's, Alzheimer's and Lou Gehrig's, which involve ROS probably due to the over-excitation of glutammic acid receptors[22;23].

The fullerenes must be chemically modified in order to be useful in aqueous systems. One way to modify the fullerenes is through the addition of hydroxyl groups (OH). To this end, fullerenes derivatized with OH species have been shown to prevent ischemia (poisoning due to lack of oxygen) which is initiated and propagated through sudden increases in ROS as tissues react to energy depletion[24;25]. Derivatized fullerenes also reduce ROS-induced neuronal apoptosis and have been proposed as a potential therapeutic for neurogenitive disorders. Other derivatives of fullerenes include hexosulfobutyl and C3, the tris malonate derivative, and polyethylene glycol (PEG).

In short, carbon fullerenes possess several characteristics that make them appealing as agents to diagnose and fight disease, especially those with ROS involvement. There is currently a large-scale surge in fullerene research by industry and academia alike. However, the studies emerging on their toxicity are still uncertain and several issues still plague the fullerene field. First, it is difficult to predict if effective levels of fullerenes can be achieved in tissues that would affect the biological response. It is also hard to predict if the fullerenes will present hazardous side effects to other tissues besides target tissues. Lastly, it cannot be predicted if the fullerenes will be immunodetected when derivatized and exposed to serum molecules.

Regulation of Type I Hypersensitivity

Allergic reactions are the result of B cell-produced, specific IgE antibody to common, normally innocuous antigens. These antigens trigger a $T_H2$ response in which naive T cells are induced to develop into $T_H2$ cells in the presence of IL-4, which appears to be derived from a specialized subset of T cells, MC and PBB. These allergen-specific $T_H2$ cells drive allergen-specific B cells to produce IgE. In simplistic terms, MC, PBB, NK cells, T cells and even B cells are responsible for driving the initial, allergen-inducing reaction through the production of IL-4, and other $T_H2$-specific cytokines which result in IgE sensitization. Re-exposure to the allergen triggers an allergic response through the release of inflammatory mediators from MC and PBB. The IgE produced binds to FceRI on MC and PBB and the release of pre-allergic mediators is induced when two or more IgE molecules are crosslinked with allergen. Indeed, most allergy medications are aimed at neutralizing (anti-histamines, H1-receptor blockers) or preventing (anti-IgE; "Omalizumab") MC and PBB FceRI responses.

MC and PBB in Asthma

Mice without MC (compared to wild type or MC-depleted mice) fail to develop asthma-like pulmonary disease when sensitized with less-aggressive immunization protocols and challenged with aerosolized allergen[26;27]. A characteristic feature of MC in asthmatic airways is their activated status. Elevated histamine, tryptase, leukotriene $C_4$ ($LTC_4$) and prostaglandin $D_2$ ($PGD_2$) levels (MC mediators) in bronchoalveolar lavage fluids, the anti-histamine-sensitive bronchospastic response to inhaled adenosine (augmentation of degranulation by submaximally stimulated MC), and the ultrastructure of MC in bronchial biopsies showing an activated phenotype support the contention that MC are actively involved in asthmatic pathogenesis.

Activated MC produce a variety of mediators capable of promoting various aspects of asthma pathogenesis. IL-4 and IL-13 facilitate $T_H2$ immunity and IgE production. Histamine, PGD2 and LTC4 increase vasopermeability and tissue edema. Histamine, $LTC_4$ and chymase stimulate mucus production. Histamine and $LTC_4$ lower the neurogenic threshold for irritant responses. $LTC_4$, IL-5, TNFα, GM-CSF and various chemokines produce inflammation and target cells involved in tissue remodeling. For example, tryptase stimulates proliferation of fibroblasts, smooth muscle, endothelial cells and epithelial cells[28]. Consequently, understanding new pathways for attenuating these cells to activating stimuli are worthwhile goals in the context of asthma and allergic diseases.

Basophils are recruited into the airways of asthmatics during the allergy season, and after an allergen challenge, such that increased numbers are found in induced sputum[29] and in endobronchial lung biopsies[30-32]. Elevated numbers of PBB also are found in post mortem lung specimens from asthmatics[33]. Basophils have long been known to participate in the late phase of the allergic response, but more recently have been demonstrated in mice to be critically involved in the delayed, chronic allergic inflammation reaction, lasting ~1 week after a single intradermal allergen challenge, even in the absence of MC[34]. Further, PBB are the predominant IL-4-producing cell 24 h after an allergen challenge[30].

MC and PBB in Arthritis

Mast cells are present in normal human synovium, but in rheumatoid arthritis (RA) and other inflammatory joint diseases this population can expand to constitute 5% or more of all synovial cells. Recent investigations in mouse models have demonstrated that mast cells have a critical role in the generation of inflammation within the joint and strongly suggest indicate that mast cells drive non-allergic immune responses, such as arthritis, as well as in allergy. MC-derived mediators cause edema, destroy connective tissue, induce lymphocyte chemotaxis and infiltration, and induce pathological fibrosis of RA joints[35-37]. Moreover, MCs are involved in angiogenesis during RA, and their proteolytic activity results in cartilage destruction and bone remodeling. Indeed MC-stabilizing compounds are shown to have a beneficial effect in a RA disease model[38]. Thus, mast cells appear to be critical cells of joint inflammation and targeting the MC may be one way to therapeutically treat inflammatory arthritis.

The Role of ROS in MC and PBB Mediator Release

The role of ROS species in MC and PBB-induced responses has not been investigated thoroughly. Most studies suggest that ROS is elevated following IgE stimulation. Work in rat basophil leukemic cells (RBL) has shown that stimulation through the high-affinity IgE receptor induces the production of ROS. Furthermore these endogenously produced oxidants have important functions in regulation of various MC responses, including degranulation, leukotriene secretion, and cytokine production[39;40]. Conversely, antioxidants that quench intracellular ROS, differentially affect two effector functions of antigen-IgE-activated rodent MC; inhibiting degranulation and augmenting cytokine production[41]. Several secretogogues induced intracellular increases of ROS levels in rodent MC[42-44], PBB[45], and human blood-derived MC[46]. It has been demonstrated that ROS generation in human PBB that had released significantly more mediators when challenged with diesel exhaust particles compared to non-challenged cells[47]. Some evidence indicates that allergic and inflammatory skin diseases like atopic dermatitis, urticaria and psoriasis are mediated by MC-initiated oxidative stress[48] while recent studies suggest anti-oxidants can reduce asthma symptoms in mice[49;50].

Prior Art

U.S. Pat. No. 5,994,410 (Chiang et al., Nov. 30, 1999) discloses the use of water-soluble fullerene derivatives for the treatment of some free radical-related medical conditions. However, the conditions do not include allergic reactions or inflammatory arthritis.

U.S. Pat. No. 6,265,443 (Choi et al., Nov. 30, 1999) describes methods of treating neuronal injury with carboxyfullerene, but does not describe the treatment of allergic reactions or inflammatory arthritis.

U.S. Pat. No. 6,331,532 (Murphy et al., Dec. 18, 2001) discloses antioxidant compounds that target mitochondria. The antioxidant moiety of the compound may be a derivatized fullerene.

US patent application 2006/0040938 (Hartnagel et al., published Feb. 23, 2006) describes substituted fullerenes and their use as antioxidants, but does not disclose their use to treat allergic reactions or inflammatory arthritis.

There is an ongoing need to provide methods of treating allergic reactions and inflammatory arthritis. The prior art has thus far failed to provide methods of treating allergic reactions or inflammatory arthritis that involve the use of fullerenes.

SUMMARY OF THE INVENTION

The invention provides novel methods to treat or prevent or alleviate the symptoms of diseases caused by MC or PBB responses. Patients or other individuals which would benefit from treatment, including humans and animals, are administered water soluble fullerene compounds (e.g., $C_{20}$-$C_{200}$, and preferably $C_{40}$-$C_{80}$ compounds such as $C_{40}$, $C_{50}$, $C_{60}$, and $C_{70}$ compounds) under conditions and in amounts sufficient to alleviate the symptoms of IgE mediated mast cell or peripheral blood basophil allergic reactions. Exemplary conditions that can be effectively treated using the process and compositions of the present invention includes Type I hypersensitivity, anaphylaxis, hay fever, asthma, arthritis, urticaria, atopic dermatitis, rashes, heart disease and multiple sclerosis. The water soluble fullerenes can be modified by pyridines, hydroxyls, cyclodextrins, polyvinylphyrrolidone, bis (monosscuinimide, N-ethyl polyamines, deriviatives of p,p'-bis(2-amino-ethyl)-diphenyl, and other compounds.

The water soluble fullerenes may also be functionalized with compounds which target mast cells or peripheral blood basophils. In an exemplary embodiment, chimeric functionalized fullerenes that target and inhibit MC and PBB cells are contemplated by the invention. These chimeric molecules comprise fullerenes to which IgE Fc or stem cell factor (SCF)-derived peptides are preferably attached. The peptides are preferably capable of binding to the Fc receptor on MC and PBB or to the c-kit receptor (which binds stem cell factor) found specifically on MC. There peptides will serve to specifically target the fullerenes to MC and PBB so that the nanomaterials have little interaction with other cell types. Upon binding of the chimera to a MC or PBB cell surface receptor via the peptide moiety, the entire chimera is engulfed by the cell, and the fullerene component of the chimera is thus internalized into the cell where it inhibits cellular activity, but does not kill the cell. Additional molecules include IgE Fc or SCF peptides with several fullerenes covalently attached.

DETAILED DESCRIPTION OF THE PREFERRED EMBODIMENTS OF THE INVENTION

Figure 1:
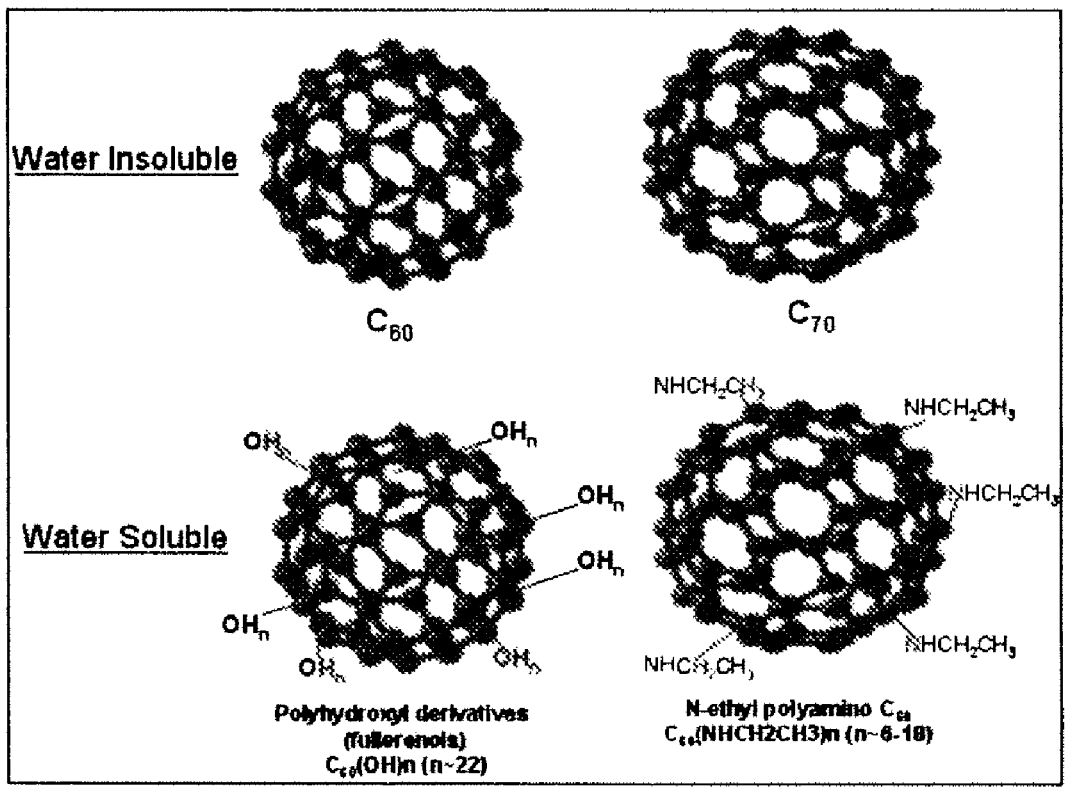
FIG. 1. Exemplary structures of fullerenes and derivatives.

The present invention is based on the discovery that water soluble fullerene nanomaterials can be used to inhibit MC and PBB mediated disease including but not limited to allergy, asthma, and arthritis. Without being bound by theory, it appears that this is due to the ability of water soluble fullerene nanomaterials to "turn off" MC and PBB allergic responses. This inhibition prevents or attenuates the increases in levels of cellular reactive oxygen species (ROS) that would otherwise occur and cause allergic inflammation, or inflammatory cascade leading to the symptoms of arthritis. The invention thus provides methods of using water soluble fullerenes to treat diseases caused by or related to MC and PBB responses. The water soluble fullerenes can range from $C_{20}$ to $C_{200}$ in size, with positive results being obtained with $C_{60}$ and $C_{70}$ fullerenes. The fullerenes can be obtained commercially from a number of sources including Buckey USA. The fullerenes used in this invention are preferably water soluble. Water solubility can be obtained by derivatizing the fullerenes with hydroxyls and other moieties, and water soluble fullerenes are commercially available. The fullerenes can be derivatized with a number of compounds, including without limitation pharmaceutically active compounds. In a particular embodiment of this invention, the water soluble fullerenes are chimeric fullerenes that specifically target MC and PBB cells.

The present invention thus provides methods for treating or preventing symptoms of diseases and conditions associated with and/or being caused, initiated, or propagated by MC and PBB soluble mediators. Examples of such diseases include but are not limited to allergic responses to external allergens such as: allergies, Type I hypersensitivity (anaphylaxis, hay fever, etc), asthma, atopic dermatitis, urticaria, rashes, etc. In addition, conditions related to autoimmune disorders may also be treated (e.g. arthritis[53;54], multiple sclerosis[55], and other autoimmune diseases[56], psoriasis, etc.). Also, treatment of diseases related to inflammation (e.g. heart disease) are is also contemplated. Those of skill in the art will recognize that, while the treatment or prevention of such conditions may be complete, i.e. all undesirable disease symptoms are either reversed or do not occur, this need not be the case. In some cases, the symptoms are lessened, attenuated or slowed, but the patient still receives a substantial benefit from the treatment. This may be particularly the case with chronic, degenerative diseases such as arthritis, multiple sclerosis, etc. where the disease may not be fully cured, but great benefit is derived by the lessening of symptoms, or by slowing of the progression of the disease.

The invention provides methods for treating or preventing such diseases and conditions in a patient by administering to the patient fullerenes that are derivatized to be water soluble. By "fullerenes that are derivatized to be water soluble" or "water soluble fullerene derivatives", we mean the molecules do not require non-physiologic solutions (e.g. xylene, benzene, etc.) for dissolution. Water soluble means that these molecules can be dissolved or dispersed in aqueous media such as phosphate buffered saline or similar physiologic buffers. Examples of such materials include but are not limited to $C_{40}$, $C_{50}$, $C_{60}$ or $C_{70}$ fullerenes. These compounds can be purchased and/or manipulated/functionalized to be water soluble using a variety of techniques including pyridinyl-appended[57], polyhydroxy addition[58], cyclodextrin, polyvinylpyrrolidone[59], bis(monosuccinimide) derivatives of p,p'-bis(2-amino-ethyl-diphehyl[60], and polyamino compounds with the number of amines typically between 10-18 units[61]. As a further reference, U.S. Pat. No. 5,994,410, the complete contents of which is hereby incorporated by reference, also provides guidance concerning the preparation of water soluble fullerenes. In one exemplary embodiment of the invention, the water soluble fullerene used in the invention is a fullerenol such as polyhydroxy $C_{60}$. In another exemplary embodiment, the water soluble fullerene is N-ethyl-polyamino $C_{60}$.

The invention also provides water soluble chimeric fullerenes that are capable of specifically targeting and inhibiting the activity of MCs and PBBs. To form these chimeric molecules, peptides that bind to an MC or PBB receptor (for example, the Fc receptor of IgE, or the c-kit receptor) are covalently attached to or associated with water soluble fullerenes. Details of an exemplary construction of a chimeric fullerene are provided in Example 7 below. Briefly, in Example 7, IgE Fc peptides that are capable of binding to the Fc receptor of IgE are coupled to derivatized (e.g. pegylated, hydroxylated) fullerenes, e.g. using standard carbodiimide chemistry. SCF-peptide chimeric fullerenes may be produced in a similar manner. Several other techniques for the addition of fullerenes to proteins and peptides have also been described[62-64]. The peptides are thereby covalently attached to the fullerene. When the fullerene-peptide chimeras are administered, upon encountering an MC or PBB, the peptides bind to counterpart receptors (i.e. a compatible or matching receptors for which they have an affinity of at least about 10-1000 μM), e.g. IgE Fc receptor-related peptides will bind to the IgE receptor on the cell surface of the MC or PBB, whereas, SCF-related peptides will bind to the c-kit receptor on MC. The receptor, mimicking its normal function when a ligand is bound, then causes the entire chimera to be taken up by the cell. As a result, the fullerene is internalized within the cell. The fullerene moiety of the engulfed chimera inhibits the normal functioning of the MC or PBB cell, resulting in a diminution of the activity of the cell. Unlike some previous methods that have been developed to target and kill MCs and PBBs, the present invention provides an advantage in that the chimeric fullerenes inhibit, but do not kill, the MCs and PBBs. Thus, crucial functions of these cells (e.g. defense against parasites) are not be totally impaired by internalization of the fullerene. Another advantage a fullerene chimeric molecule offers is reduced immunogenicity. This is due to the small size of the fullerene molecule and the fact that the attached peptides are recognized as self by the human immune system i.e. they are tolerated by the immune system, and little or no immune response is raised or elicited against the chimeras.

The invention also contemplates chimeric molecules comprising, for example, IgE Fc or SCF peptides with several fullerenes (e.g. from about 4 to 400 amino acids) covalently attached or otherwise associated with the fullerene. Further, peptides and fullerene chimeras may also be cross-linked into a network in which one or more peptides are attached to one or more different fullerenes, and/or one or more fullerenes are attached to one or more different peptides. Further, when multiple fullerenes are attached to a single peptide, the fullerenes may be the same or different. And when one or more peptides are attached to a single fullerene, the peptides may be the same or different.

Suitable IgE-Fc peptides include but are not limited to IgE Fc fragment (REFSEQ: GenBank accession NM_002001.2) can be made in a similar fashion as described previously[65]. Briefly, human genomic DNA encoding the human epsilon heavy chain CH2 through CH4 domains containing the binding sites for FceRI (CHe2-CHe3) is amplified from pAG vector containing the whole epsilon genomic DNA. The 5' end primer is 5'-GCTCGAGGGTGGAGGCGGTTCAG-GCGGAGGTGGCTCTGGCGGTGGCG GATC GTTCAC-CCCGCCCACCGTGAAG-3' (SEQ ID NO: 1), containing a flexible linker sequence and a XhoI site. The 3' end primer is 5'-GGCGGCCGCTCATTTACCGGGATTT ACAGACAC-3' (SEQ ID NO: 2), containing a NotI site. After amplification, PCR products are cloned into pCR2.1 vector and sequenced. The expression vector containing the IgE Fc fragment is transfected into SP2/0 cells and expressed in cell-culture supernatants and purified by using an anti-human IgE affinity column. Fullerenes will be attached to the ε2-4 domains via a flexible linker as see in FIGS. 7 and 8.

Suitable SCF peptides include but are not limited to protein sequences that bind c-kit (GenBank accession S80491.1). Native human $SCF^{1-141}$ is expressed as recombinant proteins in *Escherichia coli*. There is a vast amount of prior art describing the expression of recombinant $SCF^{(66-71)}$ The human SCF gene is cloned into baculovirus transfer vector pAcSecG2T under the control of the polyhedrin promoter. Sf9 cells infected with the recombinant virus express hSCF, which is purified by two-step chromatography.

The invention also provides pharmaceutical compositions containing water soluble fullerene derivatives and/or functionalized chimeric fullerenes with pharmaceutically acceptable excipients. While the water soluble fullerene derivatives and/or chimeras can be administered in the pure form, more frequently they may be administered in a pharmaceutically acceptable formulation including suitable elixirs, binders, and the like or as pharmaceutically acceptable salts or other derivatives. It should be understood that the pharmaceutically acceptable formulations include liquid and solid materials conventionally utilized to prepare liquid dosage forms (e.g. for injectable or oral administration) and solid dosage forms such as tablets and capsules. Water may be used for the preparation of liquid compositions, which may also include conventional buffers and agents to render the composition isotonic. Other potential additives include: colorants; flavorings; surfactants (TWEEN, oleic acid, etc.); and binders or encapsulants (lactose, liposomes, etc). Solid diluents and excipients include lactose, starch, conventional disintergrating agents, coatings and the like. Preservatives such as methyl paraben or benzalkium chloride may also be used. Depending on the formulation, it is expected that the active composition will consist of 1-99% of the water soluble fullerene derivatives and the vehicular "carrier" will constitute 1-99% of the composition. The pharmaceutical compositions of the present invention may include any suitable pharmaceutically acceptable additives or adjuncts to the extent that they do not hinder or interfere with the desired therapeutic effect of the water soluble fullerene derivatives.

The invention also provides a method of treating disease conditions, for example, allergic reactions or responses, asthma, immune deficiency, arthritis, multiple sclerosis, etc., which are susceptible to treatment with one or more water soluble fullerene derivatives (e.g. those that involve uptake by MC and PBB cells), or with the chimeric fullerenes of the invention. Implementation of the claimed method will generally involve identifying patients suffering from such conditions or who are likely to suffer from such conditions, or have suffered from such conditions in the past, and administering the water soluble fullerene derivative(s) and/or chimeras in an acceptable form by an appropriate route. The dosage to be administered is usually determined in Phase I clinical trials and may vary depending on the age, gender, weight and overall health status of the individual patient, as well as the nature of the disease itself, among other considerations. Administration can be oral, nasal, or parenteral, including intravenously, intramuscularly, subcutaneously, etc., or by other routes (e.g. transdermal, sublingual, aerosol, etc.). The administration of pharmaceutical compositions of the present invention can be intermittent, or at a gradual or continuous, constant or controlled rate to a patient. In addition, the time of day and the number of times per day that the pharmaceutical formulation is administered can vary. Further, the effective dose can vary depending upon factors such as the mode of delivery, gender, age, and other conditions of the patient, as well as disease type and stage.

Generally, for parenteral administration in humans, dosages in the range of from about 1 to about 100 mg of active water soluble fullerene derivative or chimera/kg of body weight/24 hr., more preferably about 5 to about 15 mg of active water soluble fullerene derivative or chimera/kg body weight/24 hr., would be effective. The level of efficacy and optimal dosage for any given water soluble fullerene derivative or chimera may vary from derivative to derivative. In addition, the water soluble fullerene derivatives and/or chimeras may be administered alone or in combination with each other, or with other therapies, e.g. antihistamines, $H_1$-receptor blockers, etc. Further, the water soluble fullerene derivatives and/or chimeric fullerenes may be administered either after the onset of symptoms (i.e. to treat symptoms that are already present), or prior to the onset of symptoms (i.e. to prevent or lessen the severity of symptoms before they are evident).

The patient that is treated by the methods of the invention will generally be a mammal. In a preferred embodiment, the mammal is a human. However, the treatment of allergic responses can also be extended to other mammals, e.g. to companion pets such as cats and dogs, to livestock, horses, and any other type of mammal that is prone to suffering from allergic reactions, arthritis, etc.

EXAMPLES

Nanotechnology, the use of nanomaterials at the molecular level, is a multidisciplinary scientific field undergoing exponential growth and has broad applications among all divisions of science. One form of nanomaterials, fullerenes, are soccerball-shaped carbon cages that can be functionalized and derivatized with a wide array of molecules. Given their unique structure and properties, fullerenes are being investigated as a new and/or improved way to diagnose, monitor, and treat certain conditions. However no studies have examined the effects these compounds have on the allergic response.

Mast cells (MC) and peripheral blood basophils (PBB) are important effector cells that have traditionally been associated with initiating and propagating the allergic response. Recent studies suggest that these cells may also be important regulators of inflammation and innate immunity. The Examples below show that fullerene nanomaterials can be used to inhibit MC and PBB responses, likely by reducing allergen-induced increases in levels of cellular reactive oxygen species (ROS).

Example 1

Effects of Fullerenes Derivatives on Cellular Viability and Growth

Figure 2:
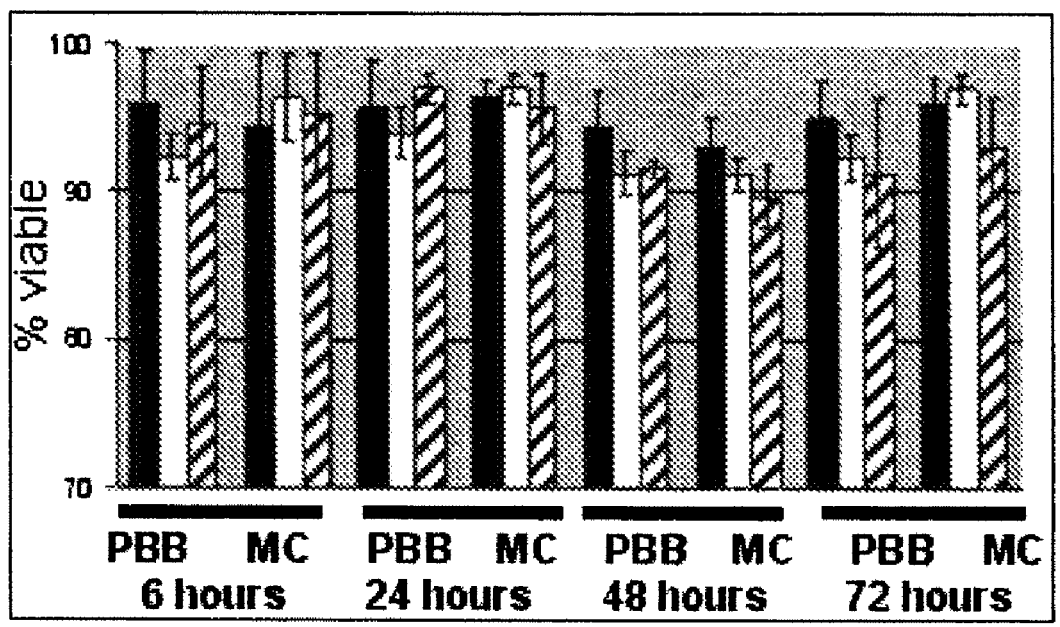
FIG. 2. A bar graph illustrating the effects of fullerenes on skin MC and PBB viability Cells were cultured with (poly; white bars, N-ethyl; striped bars) or without (black bars) fullerenes (10 mg/ml) for the indicated times. Cells were washed and viability assessed by trypan blue exclusion. Results are representative of 3 experiments from different donors. No significant differences were observed (p<0.05)

The effects of water soluble fullerene derivatives (Poly; polyhydroxy $C_{60}$ and N-ethyl; N-ethyl-polyamino $C_{60}$) on cell growth and viability were tested. Cells were incubated for up to 72 hours and total cell numbers were assessed along with trypan blue exclusion. None of the fullerenes demonstrated a significant affect on total cell numbers (not shown) or viability as shown in FIG. 2. These results suggest that fullerenes are not toxic to human MC and PBB and have no effect on their ability to proliferate.

Example 2

Fullerenes Inhibit MC and PBB Mediator Release

Figure 3:
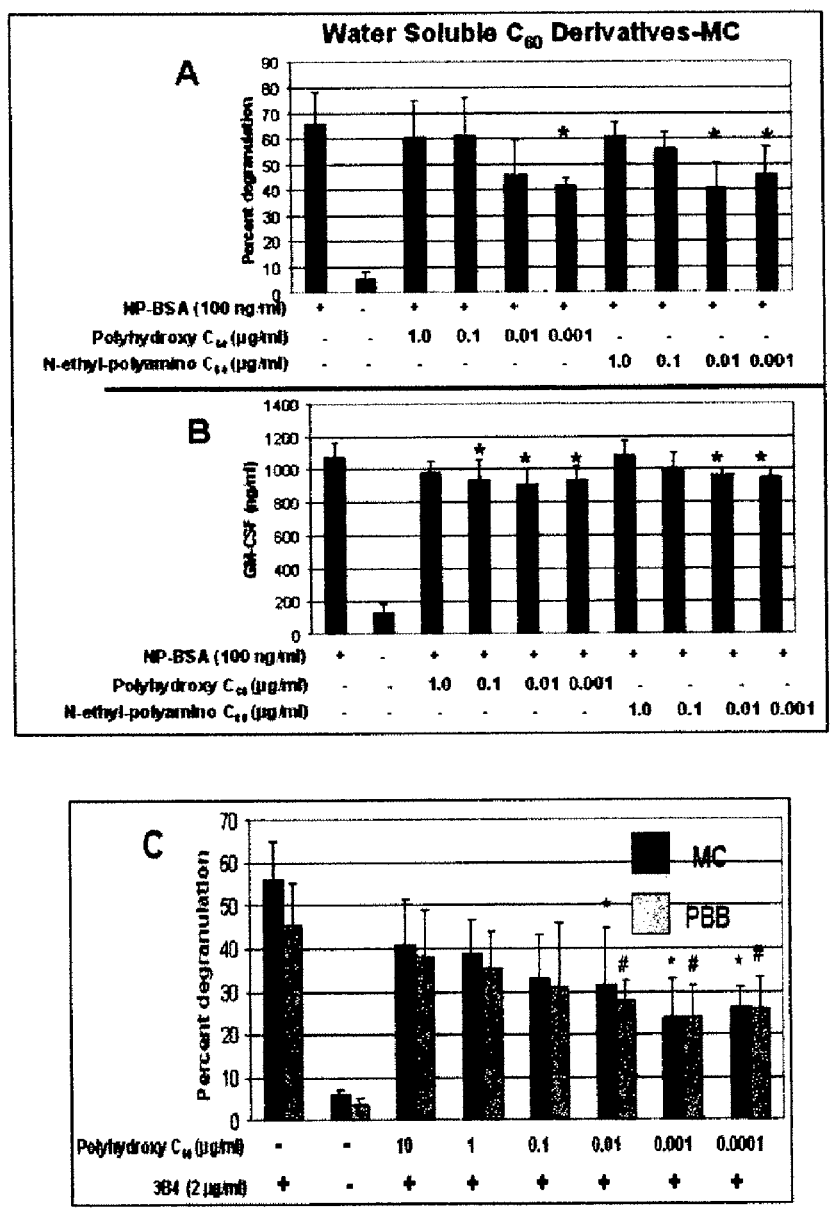
FIG. 3A-C. Bar graphs illustrating the effects of fullerenes on MC IgE-mediated degranulation and cytokine production. Skin MC were sensitized for 2 days with NP-IgE. Water soluble fullerenes were added for at least 6 hours. The cells were washed and activated with optimal concentrations of NP-BSA (100 ng/ml) for 30 minutes (A; β-hexosaminidase) or 30 hours (B; GM-CSF), centrifuged and the supernatants examined for mediator release as described previously[51;52]. In panel C, MC or PBB were incubated overnight with the indicated concentrations of fullerenes. The next day cells were washed and activated with 3B4 (anti-FcεRI receptor antibody) and the supernatants assayed for degranulation. The * indicates statistically significant changes in mediator levels compared to non-fullerene incubated cells (p<0.05).

The effects of fullerenes on antigen-induced MC and PBB mediator release were also investigated. NIP-IgE sensitized MC were incubated with varying concentrations of fullerenes before challenge with NIP-BSA. The fullerene incubation did not cause mediator release (not shown). However, when cells were incubated with water soluble fullerenes prior to challenge with optimal concentrations of antigen (100 ng/ml) there was a significant inhibition of both degranulation and cytokine production (FIG. 3A and 3B) compared to cells not incubated with the fullerenes. The water insoluble fullerenes did not significantly affect mediator release at all concentrations tested. Additionally, the inhibition occurred at several antigen concentrations tested (0.1 to 10,000 ng/ml), required at least a 4 hour incubation of the cells prior antigen challenge, and similarly occurred in PBB (not shown). The affect does not appear to simply be due to steric hindrance/interference of antigen binding to IgE as the same inhibition was observed with anti-IgE receptor antibodies using MC and PBB (FIG. 3C). These data are the first to demonstrate that water soluble fullerenes can inhibit IgE-driven mediator release from MC and PBB.

Example 3

Water Soluble Fullerenes are Endocytosed into MC

Figure 4:
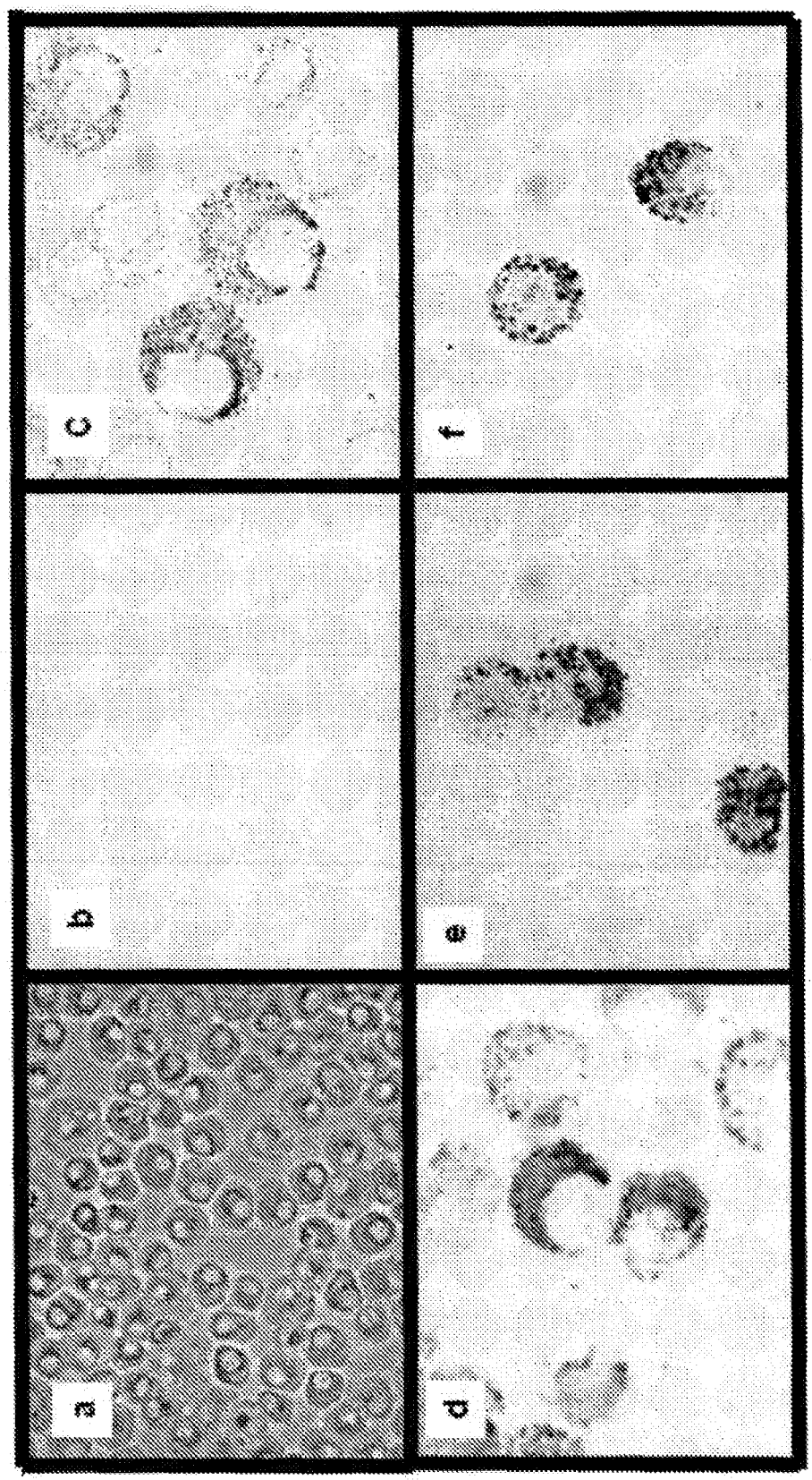
FIG. 4A-F. Photographs showing carbon fullerenes localize within the cytoplasm of MC. Skin MC (a-d) or PBB (e, f) were incubated with Polyhydroxy $C_{60}$ (10 ng/ml; a, b, c, f) or N-ethyl-polyamino $C_{60}$ (0.1 μg/ml; d, f) for 4 hours, washed and cytocentrifuged onto slides. The cytocentrifuge preparations were incubated with anti-$C_{60}$ fullerene Abs (c, d, e, f) or with an isotype-matched control (a, b) overnight. The cytospins were washed and incubated with a 1:50 dilution of peroxidase-conjugated, anti-mouse Abs and developed with AEC as described. Photographs a and b are the same field taken under phase-contrast (a) or light (b) at a magification of 400×. Pictures c-f were taken under light at a magification of 1000×.

To access the cellular localization if the fullerenes within human MC, these cells were incubated with the water soluble fullerenes and immunohistochemistry was assessed using a fullerene-specific antibody Ab (59;60). As seen in FIG. 4, skin MC incubated with the fullerenes for >2 hours reacted with the fullerene Ab. Similar staining was observed with PBB (not shown). The staining was mostly within the cytoplasm and not at the cell membrane of the cells suggesting that the fullerenes exert their inhibitory affect within the cell. Labeling with the fullerene Ab within 4 hours after fullerene incubation was observed, suggesting that these molecules are endocytosed quickly (data not shown).

Example 4

Anti-oxidant Effects of Fullerenes

Figure 5:
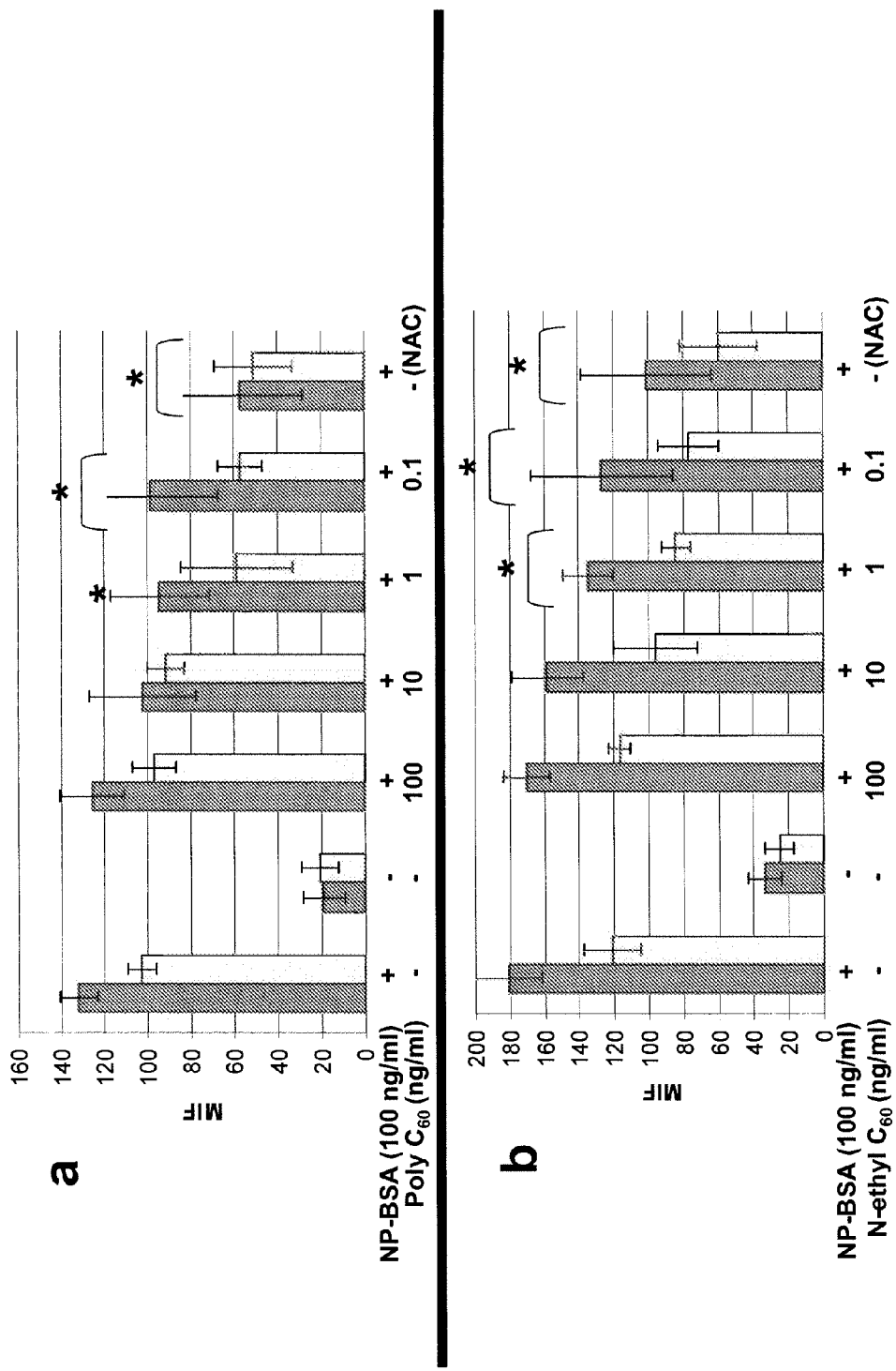
FIG. 5A-B. Bar graphs showing fullerenes inhibit ROS production in skin MC and PBB. Skin MC (grey) or PBB (white) were sensitized overnight with anti-NIP-IgE (1 μg/ml). Cells were activated for 30 min with NIP-BSA (100 ng/ml) with or without preincubation with the indicated concentrations of fullerenes or N-acetyl-L-cysteine (NAC; 10 μmol). Cellular ROS levels were detected by incubating the cells in the ROS indicating dye 5-(and-6)-carboxy-2',7'-dichlorodihydrofluorescein diacetate (DCF) followed by FACS analysis. The results are representative of 3 separate MC or PBB cultures. The * or # indicates statistically significant changes in ROS levels for MC and PBB, respectively (p<0.05). A, polyhydroxy $C_{60}$ fullerenes; B, N-ethyl-polyamine $C_{60}$ fullerenes.

Fullerenes have been shown to be powerful anti-oxidants in a variety of cell types. To investigate the mechanism by which these fullerenes inhibit allergic mediator release from skin MC and PBB, the effect these compounds have on ROS levels within the cell after antigen stimulation was tested. As seen in FIG. 5, preincubation of skin MC with fullerenes significantly reduced the levels of the ROS when the cells were challenged with optimal concentrations of antigen. This effect was comparable to that observed with NAC; a powerful anti-oxidant. These data suggest that the inhibition of MC and PBB mediator release observed with fullerene preincubation may be due in part to reductions in ROS levels after antigen challenge.

Example 5

Water Soluble Fullerenes Inhibit Antigen-Induced Anaphylaxis

Figure 6:
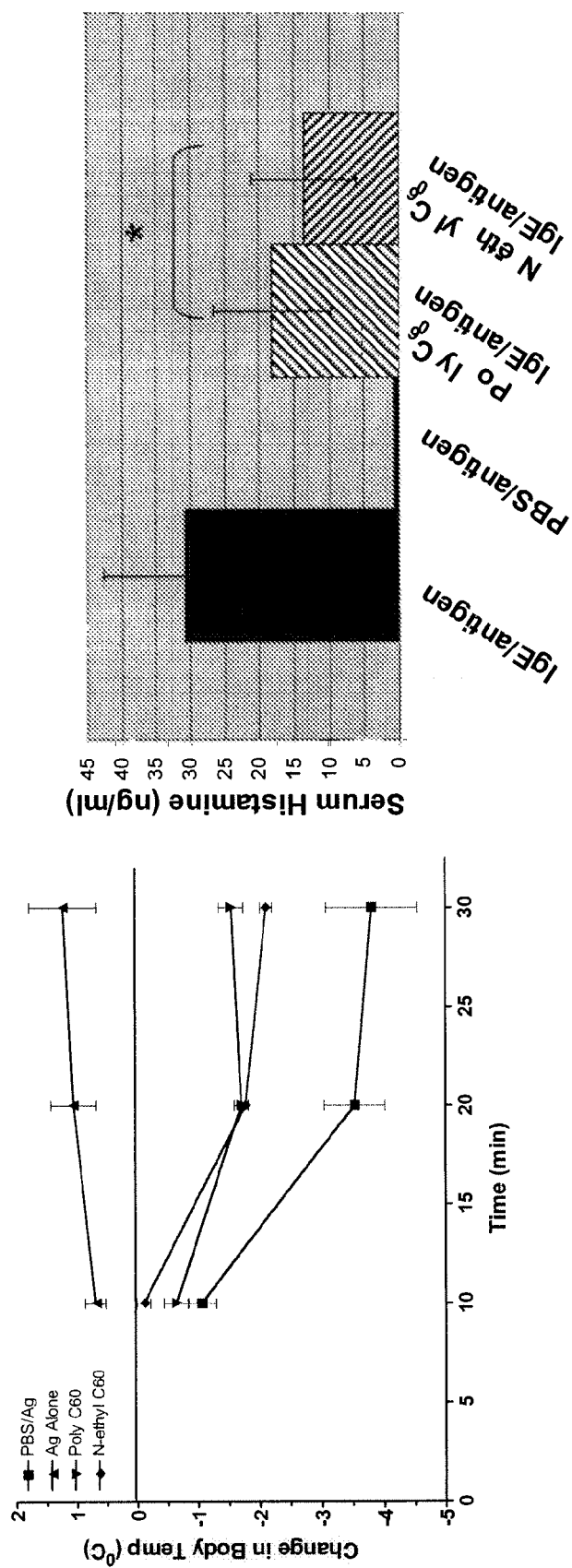
FIG. 6. Line and Bar graphs showing fullerenes inhibit IgE-induced anaphylaxis in vivo. Mice (3-5 per group; n=2 separate experiments) were sensitized with or without (Δ) DNP-IgE overnight. The mice were then given vehicle alone (■) or fullerenes (▼=Poly $C_{60}$; ●=N-ethyl $C_{60}$) intravenously (50 ng/ml) overnight. The next morning the animals were challenged with DNP-BSA (100 μg/ml) and the core body temperature measured for up to 30 minutes. Serum histamine levels were measured by ELISA. A, data represented with line graphs; B, data represented with bar graphs.

Systemic anaphylaxis is predominately driven by the activation of MC and PBB through IgE-FceRI crosslinking (45; 61). These cell types were shown to be inhibited by preincubation with fullerene derivatives. Thus, we hypothesized that they could inhibit MC and PBB-induced anaphylaxis in vivo using IgE-sensitized mice. As seen in FIG. 6, fullerenes injected intravenously into IgE-DNP-sensitized mice 24 hours prior to systemic DNP antigen challenge significantly reduced the anaphylactic reaction as measured by drop in body temperature. In addition, there was a significant reduction in serum histamine levels with the fullerene preincubation. Thus, fullerenes are capable of inhibiting IgE-mediated anaphylaxis in vitro and in vivo, which suggests that these molecules have previously unrecognized anti-allergic properties.

Example 6

Determination of the Mechanisms by Which Fullerenes Inhibit Human MC and PBB Responses The mechanisms leading to degranulation, prostaglandin, leukotriene and cytokine production may utilize differential signaling pathways leading to their release from the MC and PBB. Therefore, the mechanism of and/or optimal dose for fullerene inhibition may be different for each cell type, inflammatory mediator, and between donors. In addition, preliminary results suggest that lower doses of fullerenes (0.001 to 0.1 µg/ml) inhibits degranulation and cytokine production more effectively than higher doses. An in-depth analysis is performed to determine the optimal dose of fullerene inhibition for degranulation, leukotriene, prostaglandin, and cytokine production. In addition, similar parameters are measured for variability for each donor and comparisons are made between donors to determine potential variability in mediator release, a well documented phenomena in PBB (2) and potentially lung MC (3).

General Techniques

In order to isolate, culture and perform functional and biochemical studies with human MC (skin and lung-derived) and PBB, fresh samples of skin or lung are obtained from surgical specimens (e.g. through the Cooperative Human Tissue Network of the National Cancer Institute in Columbus, Ohio). Tissue is cut into 1- to 2-mm fragments and incubated in a solution of tissue-digesting enzymes multiple times. The dispersed cells are separated from residual tissue by filtration, red blood cells are removed and the nucleated cells suspended at $1 \times 10^6$ cells/ml in serum-free AIM-V medium (Life Technologies, Rockville, Md.) containing 100 ng/ml rhuSCF (Biosource and Amgen) in 24 well plates. Lung MC are further purified by positive selection with anti-CD117 Abs before culture.

Peripheral blood basophils are purified from buffy coats collected from healthy, non-medicated donors who had given informed consent. Basophils are partially purified by Percoll gradient centrifugation and extensively purified by negative selection as previously described (65;66).

Highly purified (>99%), fullerenes (water soluble and insoluble) are commercially available from BuckyUSA (Houston, Tex.) and Luna Nanoworks (Danville, Va.). IgE-DNP-sensitized cells are challenged with varying concentrations of fullerenes and challenged with optimal concentrations of DNP. Conversely, cells are incubated with fixed concentrations of fullerenes and challenged with varying concentrations of DNP. Experiments include appropriate positive controls (anti-IgE receptor Abs) as well as non-IgE-mediated stimuli such as compound 48/80 (skin MC), calcium ionophore (A23187), Substance P, and bacterial byproducts (f-met). The β-hexosaminidase assay and tryptase assays (to measure degranulation) and in-house ELISA to measure cytokine production are known (67;68). LTC4 and PGD2 release are measured using commercially available kits (Cayman Scientific).

Testing the Mechanisms of Inhibition Focusing on ROS-Associated Signaling Pathways.

There is increasing evidence that oxidative stress and reactive oxygen species (ROS) are involved in a large number of inflammatory responses, including asthma (69-71). Oxidative stress appears to be one of the important mechanisms involved in human MC and PBB allergic mediator release. The previous examples demonstrate that fullerenes inhibit allergic cells through mechanisms that result in a blunted ROS response. To explore the antioxidative functions of these nanoparticles, the metabolism of ROS is investogayed using ROS-specific dyes and kits. For example ROS levels are estimated by measuring dichlorodihydrofluorescein (DCF) oxidation and FACs analysis as above. The use of the anti-oxidant N-acytlcysteine (NAC; Molecular Probes) and carvedilol (Roche), as an oxidant scavenger serve as controls in all experiments.

Determination of the Cellular Localization of the Fullerenes and the Duration They Can Be Detected Within the Cell.

Data presented in the previous examples suggests that fullerenes are endocytosed into the MC and PBB where they exert their inhibitory effect. In order to confirm and extend these findings, cells are challenged with fullerenes as above and allowed to sit in culture for varying times (0 to 24 hours). Cells are washed thoroughly and FACs analysis is performed with the anti-fullerene Abs described in FIG. 4. An anti-mouse-FITC antibody (Fab2) and FACs analysis is used to show that fullerenes are not be detected on the cellular surface.

Previous studies suggest that fullerene derivatives cross the external cellular membrane and localize preferentially to the mitochondria (59;60). The fate of the fullerenes inside human MC and PBB is determined using confocal microscopy. Cells are challenged with or without fullerenes for varying time points, washed and cultured in culture medium for varying times and the fullerenes are tracked. Cytocentrifuge preparations are prepared at different time points and examined for reactivity with the anti-fullerene Abs as described above. These experiments show whether the fullerenes remain inside the cell or are cleared with time.

Co-localization to various organelles is achieved by using mitochondrial dye (Mitotracker; a red-fluorescent dye that stains mitochondria in live cells and its accumulation is dependent upon membrane potential) or lysosomal-specific dyes (Image-iT, lysosomal labeling kit; Molecular Probe). Cells are labeled dually with the organelle-specific dye followed by the FITC-labeled fullerene Ab and visualized using a Leica TCS-SP2 AOBS confocal laser scanning microscope with a spectrophotometer scan head, a high resolution Marzhauser MCX-2 motorized XY stage and 3 confocal detectors at the VCU Microscopy Facility. These experiments determine the cellular localization of the fullerenes. In addition, electron microscopy (TEM and SEM with the anti-fullerene Ab and gold-conjugated secondary Abs) is used as described previously (2;72).

Example 7

Determination of the Kinetics and Mechanisms of Inhibition Using Mouse Models of Allergic Inflammation and Gene-knockout Mice The effects water soluble fullerenes on allergic asthma and anaphylaxis in vivo are investigated. It is discovered that fullerenes inhibit MC and PBB activation in vivo resulting in a blunted asthmatic and allergic responses.

Asthma Model

Two separate but similar protocols are used to study the effects of fullerenes on the IgE-mediated allergic response following antigen challenge. In the first protocol, mice (triplicate) are exposed to a 1% ovalbumin (OA) (or phosphate-buffered saline [PBS]) solution by aerosolization for 20 min each day over 10 consecutive days (73). In the second protocol, mice are actively immunized by intraperitoneal injection of 20 μg of OA (grade V, Sigma) together with 2.0 mg of alum (Pierce, Rockford, Ill.) in 100 μl of PBS, or with PBS alone, on Day 1 and Day 14. The mice are injected with or without water soluble fullerenes the day before antigen challenge on days 24, 25, and 26 with aerosolized 1% OA-PBS solution for 20 minutes. All mice are sacrificed 48 h after their last OA exposure. To examine if fullerenes are interfering with IgE binding to the MC and/or IgE binding to the antigen, fullerenes are also simultaneously injected with IgE or antigen. The next day cells are injected LP with DNP-HSA (100 μg, Sigma-Aldrich). Several separate parameters indicative of murine asthmatic responses are measured and the differences between fullerene and non-fullerene-challenged cells are compared.

Immunoglobulins and Cytokines

Venous blood is collected from the tail vein before and at various time points during the sensitization period into serum separator tubes and stored at 20° C. Serum Ab levels are determined using standards for OA-specific IgE and IgG as previously described (73). The levels of cytokine secreted into the bronchoalveolar lavage (BAL; see below) fluid are determined by ELISA as described previously using human cytokine antibodies (74) IL-4, IL-5, and IFN-α are measured. ELISA's are performed with 100 μl of the undiluted BAL fluid from each animal. The limits of detection in the in-house ELISA range from 1 pg/ml for IL-13 to 10 pg/ml for IL-5. As standards, recombinant human and mouse cytokines are used (PharMingen and Genentech).

BAL Collection and Differential Cell Count

To collect BAL, lungs are lavaged with 1-ml aliquots of sterile PBS through a syringe attached to the tracheal cannula. Lavage fluid is centrifuged and the cell pellet as resuspended in RPMI medium. The cell-free supernatant of each BAL sample are stored at 20° C. until cytokine assay. Cells from BAL fluid are resuspended in RPMI and counted with a hemocytometer. Differential cell counts are made from cytospin preparations as described (75). Cells are identified as macrophages, eosinophils, neutrophils, and lymphocytes by standard morphology and at least 300 cells are counted under ×400 magnification. The percentage and absolute numbers of each cell type are calculated.

Immunolabeling of Eosinophils

Lung tissue is removed and fixed in 10% formalin solution. Sections (4 μm thick) are cut, deparaffinized, and treated with porcine trypsin for 30 min at 37° C. After washing and blocking with goat serum, rabbit polyclonal anti-mouse MBP is added overnight followed by FITC-conjugated goat anti-rabbit secondary antibodies. Slides are washed and stained with 1% Chromotrope 2R (Harlesco, Gibbstown, N.J.). For counting, a computer software program is used (IP Lab Spectrum, Signal Analytics, Vienna, Va.) and results are expressed as the number of positive cells per unit area as described previously (75).

Passive Systemic Anaphylaxis (PSA) Model

To test inhibition of mouse anaphylaxis, mice are injected intraperitoneally (IP) with 50 μg of DNP-specific IgE. After approximately 4 to 6 hours the mice (triplicate) are injected with or without different concentrations of fullerenes. The next day cells are injected IP with DNP-HSA (100 μg, Sigma-Aldrich). To examine if fullerenes are interfering with IgE binding to the MC and/or IgE binding to the antigen, fullerenes are simultaneously injected with IgE or antigen. Core body temperature measurements are made at the beginning of the assay, and every 10 minutes after DNP challenge, using a digital thermometer with a rectal probe. After 30 minutes, mice are sacrificed, and cardiac puncture is used to obtain plasma, from which histamine and other mediators are measured by ELISA. Peritoneal MC are collected, cytocentrifuged onto slides, and examined for the presence of fullerenes or to measure ROS activity as described above.

These investigations show that fullerenes inhibit the IgE-mediated asthmatic and allergic response. Testing in animal models of MC-induced-arthritis (76) and multiple sclerosis (64) is also carried out.

Example 8

MC and PBB-targeting Fullerenes

MC and PBB-targeting fullerenes are water soluble fullerenes "decorated" with IgE Fc peptides that bind to the Fc receptor on IgE. The affinity of this interaction is extremely high ($\sim 10^{-9}$ M) and serves as the platform due to the ability of FcεRI to internalize the complexes after binding. Previous attempts at specifically targeting and killing MC and PBB have been reported. Belostotsky et al developed a pro-apoptotic Fcε-Bak chimeric protein, targeted against cells expressing FcεRI to target and kill MC and PBB[72]. Similarly, molecules have been developed that target the MC/PBB via the IgE receptor and kill the cells with a toxin[72]. A (non-killing) MC and PBB-targeting chimeric fusion protein has also been developed. This chimeric protein homed to cells via their high expression of FcεRI and blunted functional responses via inhibitory receptors[65,73]. However, the chimera of the present invention are designed to target and inhibit, but not kill, the MC and PBB cells.

IgE is obtained from any of several sources, e.g. the JW8/1 cell line (ATCC) which secretes antigen-specific IgE. Alternatively, direct Fc fragment may be obtained by expression of the human IgE Fc fragment using a construct as described above. This construct has whole epsilon genomic DNA which can be expressed in SP2/0 cells. The Fc peptides are preferably derived from human IgE using a Fc purification kit. Alternatively, stem cell factor peptides (the ligand for c-kit found almost exclusively on MC) are used. SCF preferentially binds to the MC-specific receptor with high affinity[69]. COS cells transfected with genomic SCF are used to make large amounts of SCF and SCF peptides.

Figure 7A:
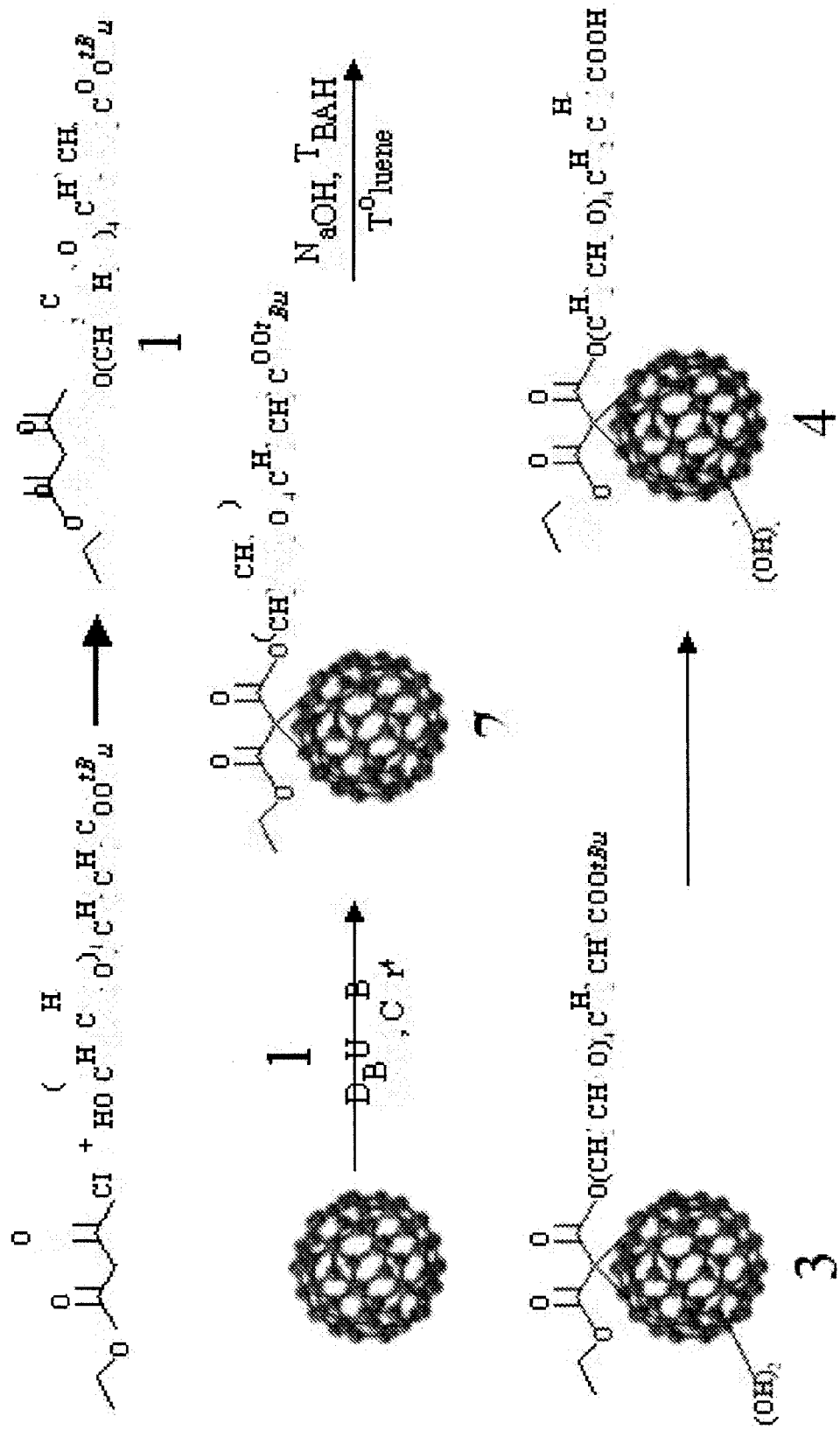
FIG. 7A and B. A, Schematic representation of functionalization (pegylation and hydroxylation) of fullerenes in order to add MC and PVV-targeting moieties; B, schematic representation of conjugation of functionalized fullerenes with Fc fragments of human IgE or stem cell factor peptides, as indicated.

The approach used to functionalize (pegylate and hydroxylate) fullerenes is illustrated in FIG. 7A. N-terminal protected polyethylene glycol ($PEG_4$; to increase water solubility) is reacted with ethyl 3-chloro-3-oxo-propionate to produce compound 1. Compound 2 is produced by coupling compound 1 to fullerenes utilizing a Bingel-Hirsh reaction. The fullerene cages were hydroxylated to produce compound 3 by refluxing in sodium hydroxide/toluene under oxidizing conditions. The tert-butyl protecting groups were removed to produce the carboxylated product (4) by performing additional hydrolysis.

Figure 7B:
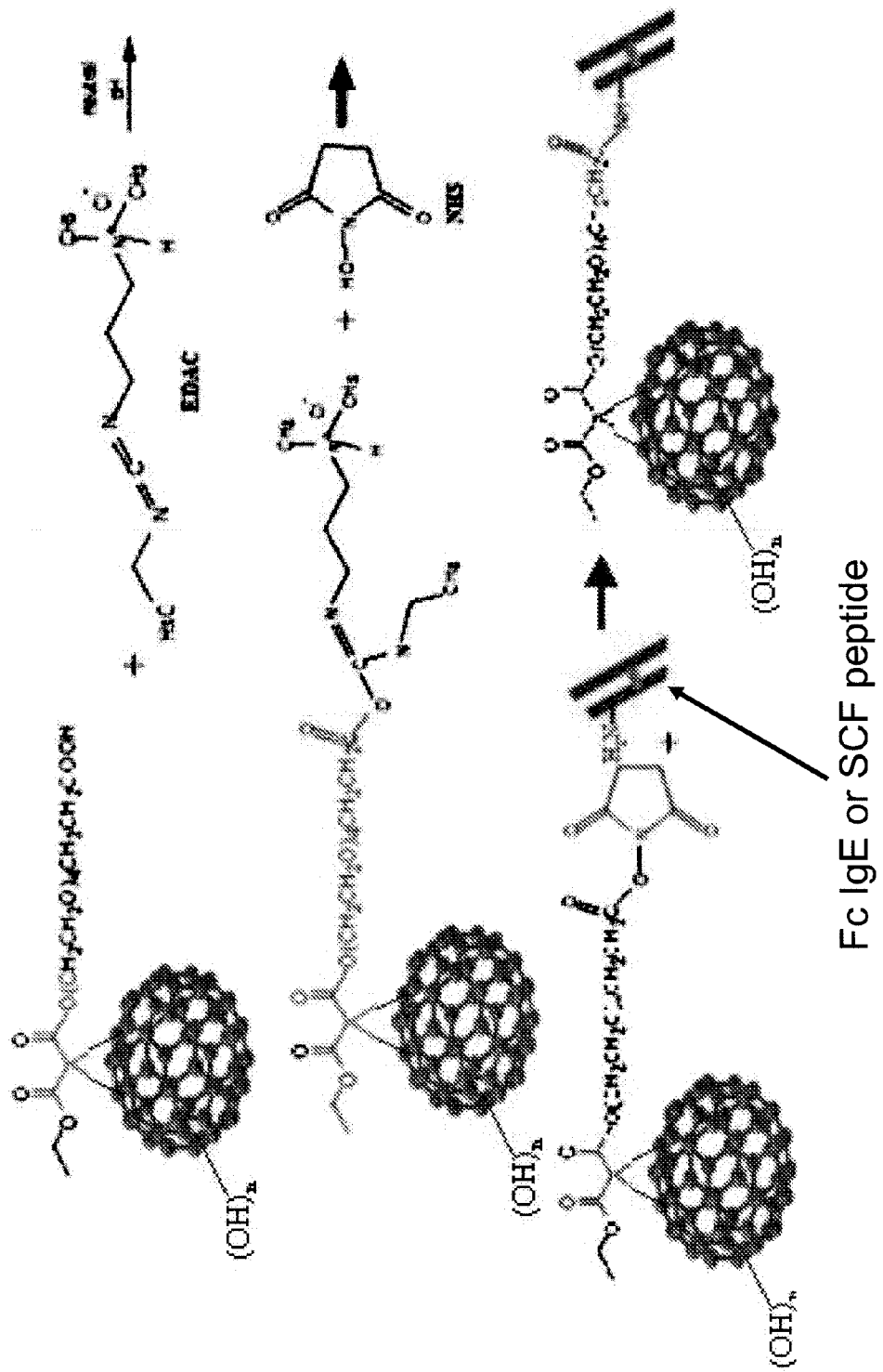

To make the fullerene/IgE-Fc or fullerene-SCF molecule, compound 4 is conjugated to IgE Fc or SCF-peptide using standard carbodiimide chemistry (see FIG. 7B). The functionalized and hydroxylated fullerenes (which are commercially available) are suspended in 50 mM MES, pH 6.8. N-hydroxysuccinimide (NHS) and 1-ethyl-3-(3-dimethylaminopropyl)carbodiimide are dissolved into the suspension and allowed to react for 24 hrs at room temperature. The activated fullerene suspension is added drop-wise to the IgE-Fc peptide in 50 mM MES, pH 6.8 and allowed to react for 5 hrs at room temperature. Fullerene/Fc-IgE or fullerene/SCF-conjugate is prepared at three different molar ratios: 75:1, 25:1, and 10:1. The conjugate samples are filtered to remove aggregates and dialyzed with PBS to remove free peptide and fullerene and tested either using FACs or immunohistochemistry with the fullerene Ab to assess binding to MC and PBB. In addition, an ELISA is developed using a combination of anti-fullerene and anti-IgE or anti-SCF Abs so that the efficacy of the conjugation procedure can be determined. Initial screening determines if the conjugates trigger cell degranulation alone.

Figure 8:
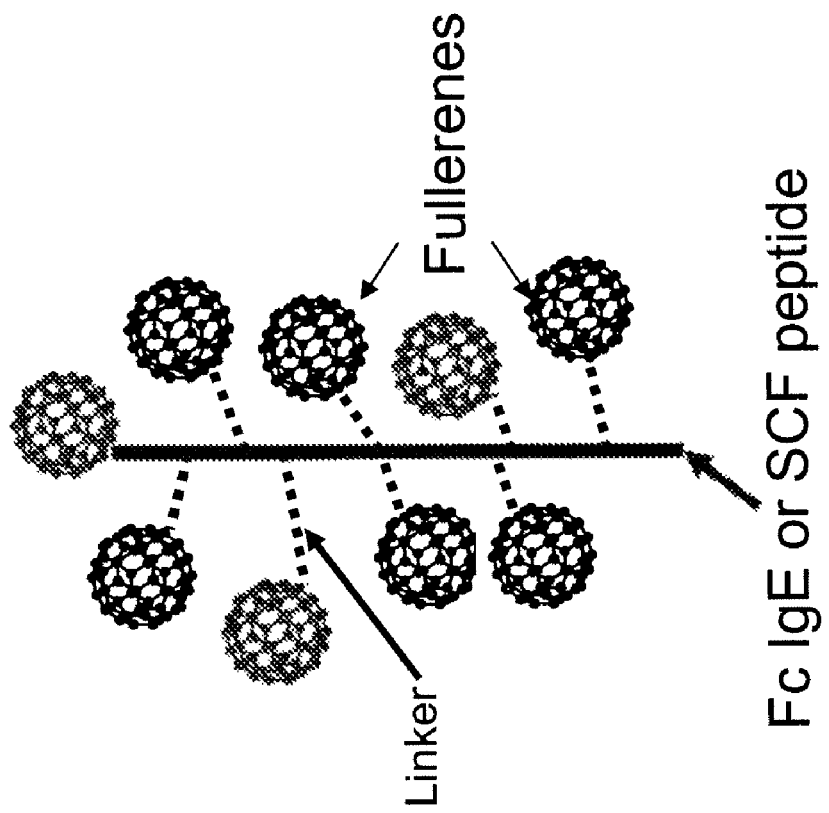
FIG. 8. Schematic representation of Fc-IgE or SCF peptide with attached fullerenes (number of fullerenes >5).

FIG. 8 shows a schematic of an IgE-FC or SCF-peptide with many fullerenes attached (the fullerenes can be the same or different in size). The linker chains can be a variety of different lengths and can take a variety of different forms (e.g., esters, ethers, peptides, oligomers, etc.). As discussed above, conjugation can be carbodiimide chemistry similar to that shown in FIG. 7B or by other suitable attachment methods.

There are several advantages of having a MC/PBB-targeting molecule that will inhibit, but not kill, the cells. While still not definitively established, most researchers agree that MC (more so than PBB) play a critical role in the defense against parasites. Thus, it is not known what the consequences would be if humans were devoid of MC. It is predicted that the chimeric proteins that target FcεRI will also target non-MC FcεRI-expressing cells. FcεRI expression has been reported on several other cell types but this expression is either intracytoplasmic or at extremely low levels. The use of SCF-conjugates helps to eliminate receptor cell promiscuity as its receptor, c-kit, is found only on MC.

Another advantage a fullerene/Fe-IgE chimeric molecule offers is reduced immunogenicity. This is due to the small size of the fullerene molecule and the fact that IgE-Fc peptide is recognized as self by the human immune system. Lastly, fullerenes have the capacity to be functionalized with a wide variety of molecules which enables the examination of many ways to increase the efficiency of MC and PBB homing and inhibition.

REFERENCES (1) Kroto H W, Allef A W, Balm S P. Buckminsterfullerene. Chem. Rev. 91, 1213-35. 1991.

(2) Moghimi S M, Hunter A C, Murray J C. Long-circulating and target-specific nanoparticles: theory to practice. Pharmacol Rev 2001; 53(2):283-318.

(3) Moghimi S M, Hunter A C, Murray J C. Nanomedicine: current status and future prospects. FASEB J 2005; 19(3): 311-30.

(4) Shaffer C. Nanomedicine transforms drug delivery. Drug Discov Today 2005; 10(23-24):1581-2.

(5) Staniloae C S, Ambrose J A. Identification of vulnerable atherosclerotic plaques. Expert Rev Cardiovasc Ther 2003; 1(3):353-65.

(6) Moghimi S M, Szebeni J. Stealth liposomes and long circulating nanoparticles: critical issues in pharmacokinetics, opsonization and protein-binding properties. Prog Lipid Res 2003; 42(6):463-78.

(7) Lanza G M, Winter P M, Caruthers S D, Morawski A M, Schmieder A H, Crowder K C et al. Magnetic resonance molecular imaging with nanoparticles. J Nucl Cardiol 2004; 11(6):733-43.

(8) Emerich D F, Thanos C G. Nanotechnology and medicine. Expert Opin Biol Ther 2003; 3(4):655-63.

(9) Mori T, Takada H, Ito S, Matsubayashi K, Miwa N, Sawaguchi T. Preclinical studies on safety of fullerene upon acute oral administration and evaluation for no mutagenesis. Toxicology 2006; 225(1):48-54.

(10) Worle-Knirsch J M, Pulskamp K, Krug H F. Oops they did it again! Carbon nanotubes hoax scientists in viability assays. Nano Lett 2006; 6(6):1261-8.

(11) Magrez A, Kasas S, Salicio V, Pasquier N, Seo J W, Cello M et al. Cellular toxicity of carbon-based nanomaterials. Nano Lett 2006; 6(6):1121-5.

(12) Fiorito S, Serafino A, Andreola F, Togna A, Togna G. Toxicity and biocompatibility of carbon nanoparticles. J Nanosci Nanotechnol 2006; 6(3):591-9.

(13) Fenoglio I, Tomatis M, Lison D, Muller J, Fonseca A, Nagy J B et al. Reactivity of carbon nanotubes: free radical generation or scavenging activity? Free Radic Biol Med 2006; 40(7):1227-33.

(14) Sayes C M, Gobin A M, Ausman K D, Mendez J, West J L, Colvin V L. Nano-C60 cytotoxicity is due to lipid peroxidation. Biomaterials 2005; 26(36):7587-95.

(15) Sayes C M, Liang F, Hudson J L, Mendez J, Guo W, Beach J M et al. Functionalization density dependence of single-walled carbon nanotubes cytotoxicity in vitro. Toxicol Lett 2006; 20;161(2):135-42.

(16) Fumelli C, Marconi A, Salvioli S, Straface E, Malomi W, Offidani A M et al. Carboxyfullerenes protect human keratinocytes from ultraviolet-B-induced apoptosis. J Invest Dermatol 2000; 115(5):835-41.

(17) Monti D, Moretti L, Salvioli S, Straface E, Malomi W, Pellicciari R et al. C60 carboxyfullerene exerts a protective activity against oxidative stress-induced apoptosis in human peripheral blood mononuclear cells. Biochem Biophys Res Commun 2000; 277(3):711-7.

(18) Shvedova A A, Kisin E R, Mercer R, Murray A R, Johnson V J, Potapovich A I et al. Unusual inflammatory and fibrogenic pulmonary responses to single-walled carbon nanotubes in mice. Am J Physiol Lung Cell Mol Physiol 2005; 289(5):L698-L708.

(19) Yamawaki H, Iwai N. Cytotoxicity of water soluble fullerene in vascular endothelial cells. Am J Physiol Cell Physiol 2006;

(20) Rouse J G, Yang J, Barron A R, Monteiro-Riviere N A. Fullerene-based amino acid nanoparticle interactions with human epidermal keratinocytes. Toxicol In Vitro 2006;

(21) Bosi S, Da Ros T, Spalluto G, Prato M. Fullerene derivatives: an attractive tool for biological applications. Eur J Med Chem 2003; 38(11-12):913-23.

(22) Dugan L L, Turetsky D M, Du C, Lobner D, Wheeler M, Almli C R et al. Carboxyfullerenes as neuroprotective agents. Proc Natl Acad Sci USA 1997; 19;94(17):9434-9.

(23) Dugan L L, Lovett E G, Quick K L, Lotharius J, Lin T T, O'Malley K L. Fullerene-based antioxidants and neurodegenerative disorders. Parkinsonism Relat Disord 2001; 7(3):243-6.

(24) Lai Y L, Chiou W Y, Lu F J, Chiang L Y. Roles of oxygen radicals and elastase in citric acid-induced airway constriction of guinea-pigs. Br J Pharmacol 1999; 126(3):778-84.

(25) Lai Y L, Chiang L Y. Water-soluble fullerene derivatives attenuate exsanguination-induced bronchoconstriction of guinea-pigs. J Auton Pharmacol 1997; 17(4):229-35.

(26) Williams C M, Galli S J. Mast cells can amplify airway reactivity and features of chronic inflammation in an asthma model in mice. J Exp Med 2000; 192(3):455-62.

(27) Kobayashi T, Miura T, Haba T, Sato M, Serizawa I, Nagai H et al. An essential role of mast cells in the development of airway hyperresponsiveness in a murine asthma model. J Immunol 2000; 164(7):3855-61.

(28) Schwartz L B. Effector cells of anaphylaxis: mast cells and basophils. Novartis Found Symp 2004; 257:65-74; discussion 74-9, 98-100, 276-85:65-74.

(29) Gauvreau G M, Lee J M, Watson R M, Irani A M, Schwartz L B, O'Byrne P M. Increased numbers of both airway basophils and mast cells in sputum after allergen inhalation challenge of atopic asthmatics. Am J Respir Crit Care Med 2000; 161(5):1473-8.

(30) Nouri-Aria K T, Irani A M, Jacobson M R, O'brien F, Varga E M, Till S J et al. Basophil recruitment and IL-4 production during human allergen-induced late asthma. J Allergy Clin Immunol 2001; 108(2):205-11.

(31) Irani A M, Huang C, Xia H Z, Kepley C, Nafie A, Fouda E D et al. Immunohistochemical detection of human basophils in late-phase skin reactions. J Allergy Clin Immunol 1998; 101(3):354-62.

(32) Macfarlane A J, Kon O M, Smith S J, Zeibecoglou K, Khan L N, Barata L T et al. Basophils, eosinophils, and mast cells in atopic and nonatopic asthma and in late-phase allergic reactions in the lung and skin. J Allergy Clin Immunol 2000; 105(1 Pt 1):99-107.

(33) Kepley C L, McFeeley P J, Oliver J M, Lipscomb M F. Immunohistochemical detection of human basophils in postmortem cases of fatal asthma. Am J Respir Crit Care Med 2001; 164(6):1053-8.

(34) Mukai K, Matsuoka K, Taya C, Suzuki H, Yokozeki H, Nishioka K et al. Basophils play a critical role in the development of IgE-mediated chronic allergic inflammation independently of T cells and mast cells. Immunity 2005; 23(2):191-202.

(35) Woolley D E. The mast cell in inflammatory arthritis. N Engl J Med 2003; 348(17):1709-11.

(36) Maruotti N, Crivellato E, Cantatore F P, Vacca A, Ribatti D. Mast cells in rheumatoid arthritis. Clin Rheumatol 2006;

(37) Woolley D E, Tetlow L C. Mast cell activation and its relation to proinflammatory cytokine production in the rheumatoid lesion. Arthritis Res 2000; 2(1):65-74.

(38) Kobayashi Y, Okunishi H. Mast cells as a target of rheumatoid arthritis treatment. Jpn J Pharmacol 2002; 90(1):7-11.

(39) Suzuki Y, Yoshimaru T, Matsui T, Inoue T, Niide O, Nunomura S et al. Fc epsilon RI signaling of mast cells activates intracellular production of hydrogen peroxide: role in the regulation of calcium signals. J Immunol 2003; 171 (11):6119-27.

(40) Brooks A C, Whelan C J, Purcell W M. Reactive oxygen species generation and histamine release by activated mast cells: modulation by nitric oxide synthase inhibition. Br J Pharmacol 1999; 128(3):585-90.

(41) Chen S, Gong J, Liu F, Mohammed U. Naturally occurring polyphenolic antioxidants modulate IgE-mediated mast cell activation. Immunology 2000; 100(4):471-80.

(42) Matsui T, Suzuki Y, Yamashita K, Yoshimaru T, Suzuki-Karasaki M, Hayakawa S et al. Diphenyleneiodonium prevents reactive oxygen species generation, tyrosine phosphorylation, and histamine release in RBL-2H3 mast cells. Biochem Biophys Res Commun 2000; 276(2):742-8.

(43) Wolfreys K, Oliveira D B. Alterations in intracellular reactive oxygen species generation and redox potential modulate mast cell function. Eur J Immunol 1997; 27(1):297-306.

(44) Swindle E J, Hunt J A, Coleman J W. A comparison of reactive oxygen species generation by rat peritoneal macrophages and mast cells using the highly sensitive real-time chemiluminescent probe pholasin: inhibition of antigen-induced mast cell degranulation by macrophage-derived hydrogen peroxide. J Immunol 2002; 169(10):5866-73.

(45) Yoshimaru T, Suzuki Y, Matsui T, Yamashita K, Ochiai T, Yamaki M et al. Blockade of superoxide generation prevents high-affinity immunoglobulin E receptor-mediated release of allergic mediators by rat mast cell line and human basophils. Clin Exp Allergy 2002; 32(4):612-8.

(46) Swindle E J, Metcalfe D D, Coleman J W. Rodent and human mast cells produce functionally significant intracellular reactive oxygen species but not nitric oxide. J Biol Chem 2004; 19;279(47):48751-9.

(47) Kepley C L, Lauer F T, Oliver J M, Burchiel S W. Environmental polycyclic aromatic hydrocarbons, benzo(a) pyrene (BaP) and BaP-quinones, enhance IgE-mediated histamine release and IL-4 production in human basophils. Clin Immunol 2003; 107(1):10-9.

(48) Okayama Y. Oxidative stress in allergic and inflammatory skin diseases. Curr Drug Targets Inflamm Allergy 2005; 4(4):517-9.

(49) Lee K S, Kim S R, Park S J, Min K H, Lee K Y, Jin S M et al. Antioxidant down-regulates IL-18 expression in asthma. Mol Pharmacol 2006;

(50) Lee K S, Park H S, Park S J, Kim S R, Min K H, Jin S M et al. An antioxidant modulates expression of receptor activator of NF-kappaB in asthma. Exp Mol Med 2006; 38(3):217-29.

(51) Kepley C L, Pfeiffer J R, Schwartz L B, Wilson B S, Oliver J M. The identification and characterization of umbilical cord blood-derived human basophils. J Leukoc Biol 1998; 64(4):474-83.

(52) Kepley C L, Wilson B S, Oliver J M. Identification of the Fc epsilonRI-activated tyrosine kinases Lyn, Syk, and Zap-70 in human basophils. J Allergy Clin Immunol 1998; 102(2):304-15.

(53) Nigrovic P A, Lee D M. Mast cells in autoantibody responses and arthritis. Novartis Found Symp 2005; 271:200-9; discussion 210-4:200-9.

(54) Nigrovic P A, Lee D M. Mast cells in inflammatory arthritis. Arthritis Res Ther 2005; 7(1):1-11.

(55) Brown M A, Tanzola M B, Robbie-Ryan M. Mechanisms underlying mast cell influence on EAE disease course. Mol Immunol 2002; 38(16-18):1373-8.

(56) Gregory G D, Brown M A. Mast cells in allergy and autoimmunity: implications for adaptive immunity. Methods Mol Biol 2006; 315:35-50:35-50.

(57) Troshin et al. Some novel synthetic approaches to water soluble fullerene derivatives. Biological aspects of carbon clusters, P179. 2006. Ref Type: Generic

(58) Tsai M C, Chen Y H, Chiang L Y. Polyhydroxylated C60, fullerenol, a novel free-radical trapper, prevented hydrogen peroxide- and cumene hydroperoxide-elicited changes in rat hippocampus in-vitro. J Pharm Pharmacol 1997; 49(4):438-45.

(59) Yamakoshi Y N, Yagami T, Sueyoshi S, Miyata N. Acridine Adduct of [60] Fullerene with Enhanced DNA-Cleaving Activity. J Org Chem 1996; 61(21):7236-7.

(60) Schinazi R F, Sijbesma R, Srdanov G, Hill C L, Wudl F. Synthesis and virucidal activity of a water-soluble, configurationally stable, derivatized C60 fullerene. Antimicrob Agents Chemother 1993; 37(8):1707-10.

(61) Wudl et. al. Fullerenes: Synthesis Properties and Chemistry of Large Carbon Clusters. 161. 2002. G. S. Hammond, V., J. Kuck, eds, ACS.

(62) Pantarotto D, Partidos C D, Graff R, Hoebeke J, Briand J P, Prato M et al. Synthesis, structural characterization, and immunological properties of carbon nanotubes functionalized with peptides. J Am Chem Soc 2003; 125(20):6160-4.

(63) Jin H, Chen W Q, Tang X W, Chiang L Y, Yang C Y, Schloss J V et al. Polyhydroxylated C(60), fullerenols, as glutamate receptor antagonists and neuroprotective agents. J Neurosci Res 2000; 62(4):600-7.

(64) Friedman S H, Ganapathi P S, Rubin Y, Kenyon G L. Optimizing the binding of fullerene inhibitors of the HIV-1 protease through predicted increases in hydrophobic desolvation. J Med Chem 1998; 41(13):2424-9.

(65) Zhu D, Kepley C L, Zhang M, Zhang K, Saxon A. A novel human immunoglobulin Fc gamma Fc epsilon bifunctional fusion protein inhibits Fc epsilon RI-mediated degranulation. Nat Med 2002; 8(5):518-21.

(66) Blechman J M, Lev S, Brizzi M F, Leitner O, Pegoraro L, Givol D et al. Soluble c-kit proteins and antireceptor monoclonal antibodies confine the binding site of the stem cell factor. J Biol Chem 1993; 268(6):4399-406.

(67) Blechman J M, Lev S, Barg J, Eisenstein M, Vaks B, Vogel Z et al. The fourth immunoglobulin domain of the stem cell factor receptor couples ligand binding to signal transduction. Cell 1995; 80(1):103-13.

(68) Furitsu T, Tsujimura T, Tono T, Ikeda H, Kitayama H, Koshimizu U et al. Identification of mutations in the coding sequence of the proto-oncogene c-kit in a human mast cell leukemia cell line causing ligand-independent activation of c-kit product. J Clin Invest 1993; 92(4):1736-44.

(69) Philo J S, Wen J, Wypych J, Schwartz M G, Mendiaz E A, Langley K E. Human stem cell factor dimer forms a complex with two molecules of the extracellular domain of its receptor, Kit. J Biol Chem 1996; 271(12):6895-902.

(70) Jiang X, Gurel O, Mendiaz E A, Steams G W, Clogston C L, Lu H S et al. Structure of the active core of human stem cell factor and analysis of binding to its receptor kit. EMBO J 2000; 19(13):3192-203.

(71) Han J, Yan X, Zhu J, Zhi X, Zang Y, Shen B et al. Expression of a novel recombinant dual human stem cell factor in insect cells. Protein Expr Purif 2003; 31(2):311-7.

(72) Belostotsky R, Lorberboum-Galski H. Apoptosis-inducing human-origin Fcepsilon-Bak chimeric proteins for targeted elimination of mast cells and basophils: a new approach for allergy treatment. J Immunol 2001; 167(8):4719-28.

(73) Zhu D, Kepley C L, Zhang K, Terada T, Yamada T, Saxon A. A chimeric human-cat fusion protein blocks cat-induced allergy. Nat Med 2005; 11(4):446-9.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of treating symptoms of an IgE-mediated mast cell or peripheral blood basophil allergic response in a patient in need thereof, comprising the step of
administering to said patient a fullerene that is covalently modified to be water-soluble in an amount sufficient to alleviate said symptoms of said IgE-mediated mast cell or peripheral blood basophil allergic response,
wherein said fullerene that is covalently modified to be water-soluble is a water soluble $C_{40}$, $C_{50}$, $C_{60}$ or $C_{70}$ fullerene modified by covalent attachment of one or more moieties selected from the group consisting of pyridine, hydroxyl, cyclodextrin, polyvinylpyrrolidone, bis(monosuccinimide, p,p'-bis(2-amino-ethyl)-diphenyl, polyamines, and N-ethyl polyamines; and
wherein said IgE-mediated mast cell or peripheral blood basophil allergic response is selected from the group consisting of allergies, Type I hypersensitivity, anaphylaxis, and hay fever.

2. The method of claim 1, wherein said fullerene that is covalently modified to be water-soluble is functionalized with one or more agents which target mast cells or peripheral blood basophils, and wherein said one or more agents is selected from IgE Fc peptides and stem cell factor (SCF) peptides.

3. A method of inhibiting, in a patient in need thereof, a mast cell or peripheral blood basophil allergic response, comprising the step of
administering to said patient a fullerene that is covalently modified to be water-soluble in an amount sufficient to inhibit said IgE-mediated mast cell or peripheral blood basophil allergic response,
wherein said fullerene that is covalently modified to be water-soluble is a water soluble $C_{40}$, $C_{50}$, $C_{60}$ or $C_{70}$ fullerene modified by covalent attachment of one or more moieties selected from the group consisting of pyridine, hydroxyl, cyclodextrin, polyvinylpyrrolidone, bis(monosuccinimide, p,p'-bis(2-amino-ethyl)-diphenyl, polyamines, and N-ethyl polyamines; and
wherein said IgE-mediated mast cell or peripheral blood basophil allergic response is selected from the group consisting of allergies, Type I hypersensitivity, anaphylaxis, hay fever, and asthma.

4. The method of claim 3, wherein said fullerene that is covalently modified to be water-soluble is functionalized with one or more agents which target mast cells or peripheral blood basophils, and wherein said one or more agents is selected from IgE Fc peptides and stem cell factor (SCF) peptides.

5. The method of claim 1, wherein administration of said fullerene is oral via a liquid, tablet or capsule.

6. The method of claim 1, wherein administration of said fullerene is parenteral via a method selected from the group consisting of intravenous, intramuscular, and subcutaneous.

7. The method of claim 3, wherein administration of said fullerene is oral via a liquid, tablet or capsule.

8. The method of claim 3, wherein administration of said fullerene is parenteral via a method selected from the group consisting of intravenous, intramuscular, and subcutaneous.

* * * * *

SEQUENCE LISTING

```
<160> NUMBER OF SEQ ID NOS: 2

<210> SEQ ID NO 1
<211> LENGTH: 73
<212> TYPE: DNA
<213> ORGANISM: Artificial
<220> FEATURE:
<223> OTHER INFORMATION: synthetic oligonucleotide primer

<400> SEQUENCE: 1
gctcgagggt ggaggcggtt caggcggagg tggctctggc ggtggcggat cgttcacccc      60
gcccaccgtg aag                                                        73

<210> SEQ ID NO 2
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 2
ggcggccgct catttaccgg gatttacaga cac                                  33
```